(12) United States Patent
Hazard et al.

(10) Patent No.: US 8,151,799 B1
(45) Date of Patent: Apr. 10, 2012

(54) MOUTHPIECE FOR OPENING NASAL PASSAGES

(76) Inventors: James T. Hazard, Louisville, KY (US); Max M. Behr, Louisville, KY (US)

( * ) Notice: Subject to any disclaimer, the term of this patent is extended or adjusted under 35 U.S.C. 154(b) by 161 days.

(21) Appl. No.: 12/579,441

(22) Filed: Oct. 15, 2009

(51) Int. Cl.
*A61F 5/56* (2006.01)
(52) U.S. Cl. ........ 128/859; 128/848; 128/861; 128/862; 433/6; 433/140
(58) Field of Classification Search ................... 128/848, 128/859, 861, 862; 433/6, 140; D24/156, D24/181
See application file for complete search history.

(56) References Cited

U.S. PATENT DOCUMENTS

| 1,483,694 | A | 2/1924 | Stukey |
| 4,304,227 | A | 12/1981 | Samelson |
| 5,467,783 | A | 11/1995 | Meade |
| 6,694,970 | B2 | 2/2004 | Spinelli et al. |
| 7,571,727 | B2 * | 8/2009 | Croll ............................. 128/859 |
| 2004/0177852 | A1 * | 9/2004 | Abramson ..................... 128/848 |
| 2005/0284489 | A1 * | 12/2005 | Ambis ........................... 128/859 |
| 2008/0193897 | A1 | 8/2008 | Kubo et al. |

* cited by examiner

*Primary Examiner* — Patricia Bianco
*Assistant Examiner* — Caitlin Carreiro
(74) *Attorney, Agent, or Firm* — Middleton Reutlinger; Charles G. Lamb (57) ABSTRACT

A breathing device for intra-oral use particularly useful to increase the air flow through the nares, the nasal passages, pharynx, and larynx of a user includes a generally U-shaped member curved in an arch to conform to a user's upper dentition, edentulous maxillary ridges, or any prosthetic device. The U-shaped member is provided with at least one wall having a depth slightly greater than the vertical dimension of a user's upper dentition and a receptacle to receive the upper dentition, edentulous ridge, or prosthetic device. A pair of nasal passage expansion members is disposed along opposed sides of the U-shaped member and are positioned to extend into the muco-buccal and muco-labial vestibule of a user distally from the lateral extent of the nares to the zygoma whereby upon insertion of the breathing device into the mouth of a user, the walls of the muco-buccal and muco-labial vestibule engage the muscles of facial expression thereby enlarging the nares and nasal passages of a user resulting in an increase of air flow and air velocity into the nasal passages, pharynx, larynx and respiratory system.

6 Claims, 8 Drawing Sheets

MOUTHPIECE FOR OPENING NASAL PASSAGES

PRIOR ART

The present invention relates generally to a mouthpiece device for opening nasal passages and more particularly to an intra-oral device having a configuration adapted to engage selected portions in the upper jaw area of a user's mouth to engage with selected portions therein, thereby increasing the opening of the nares and the nasal passages.

During physical activity, the playing of sports and other functions including sleep (with concomitant aberrations such as snoring) which involves the respiratory system, one major concern is the amount of oxygen which is available to the body. Specifically, during physical exertion, athletes generally find that in these strenuous endeavors they are not taking in enough air to continue the activities and therefore become exhausted and need to take breaks in order to recover their systemic oxygen depletion and improve their respiratory condition. Therefore, there is a need for a device for improving the intake of air during strenuous physical activity or exercise. Moreover, persons who are confronted with snoring, sleep apnea, and other hypoxic conditions could ameliorate these conditions with a larger volume of air. One way to improve the volume of air to a human is to increase the opening of the nares and nasal passages which thereby provides the means for improved quantities of air into the respiratory system.

There is one patented suggestion for opening nasal passages which includes the use of a strip of material across the human nose, allegedly increasing the opening of the nasal passages. This device is set forth in U.S. Pat. No. 6,694,970.

SUMMARY OF THE INVENTION

It is an object of the present invention to provide a device for opening the nares and nasal passages to improve and increase respiratory functions.

Another object of the present invention is to provide a device that will decrease air flow resistance thereby increasing air flow efficiency including air flow velocity and air flow volume through the nasal passages, pharynx, and larynx and into the lungs.

It is even a further object of the present invention to provide a device that will decrease nasal and laryngeal obstruction during normal respiration, exercise and sleep.

It is even another object of the present invention to provide a device that will improve protection to the upper dentition and the vestibular areas during contact sports.

More particularly, the present invention is directed to a mouthpiece for intra-oral use which includes a generally U-shaped member curved in an arch to conform to a user's upper maxilla, including the user's natural teeth, edentulous ridge, or any prosthetic dental device. The U-shaped member includes at least one U-shaped wall with a horizontally extending platform adapted to receive a user's upper maxilla with teeth, edentulous ridge, or prosthetic device. The U-shaped wall on the labial-buccal side extends into the vestibule at a depth slightly greater than the vertical dimension of the user's upper maxillary teeth on the buccal side. A pair of nasal passage expansion members are disposed along upper portions of opposed sides of the U-shaped wall and are adapted to extend into the muco-labial vestibule of a user distally from the lateral extent of the nares to the zygoma and engage the area between the maxillary ridge, the muco-buccal vestibule, and the muscles of facial expression, whereby upon insertion into the mouth of the user, the lateral walls of the nasal passages and nares are enlarged.

A better understanding of the invention may be obtained by consideration of the drawings and the details of preferred embodiments set forth hereinafter.

DESCRIPTION OF A PREFERRED EMBODIMENT

Figure 1:
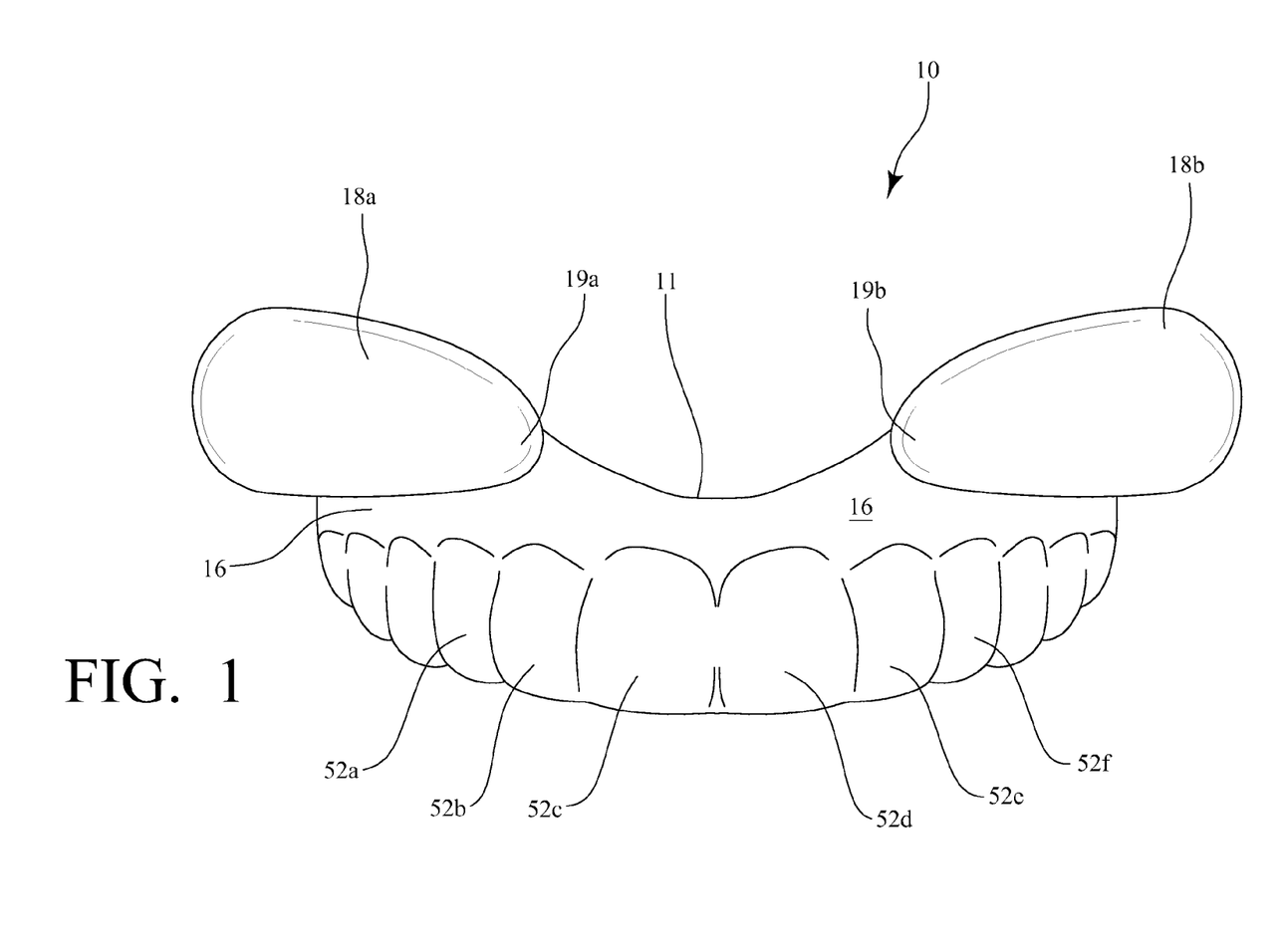
FIG. 1 is a front elevation of a preferred embodiment of the mouthpiece breathing device of the present invention.
Figure 2:
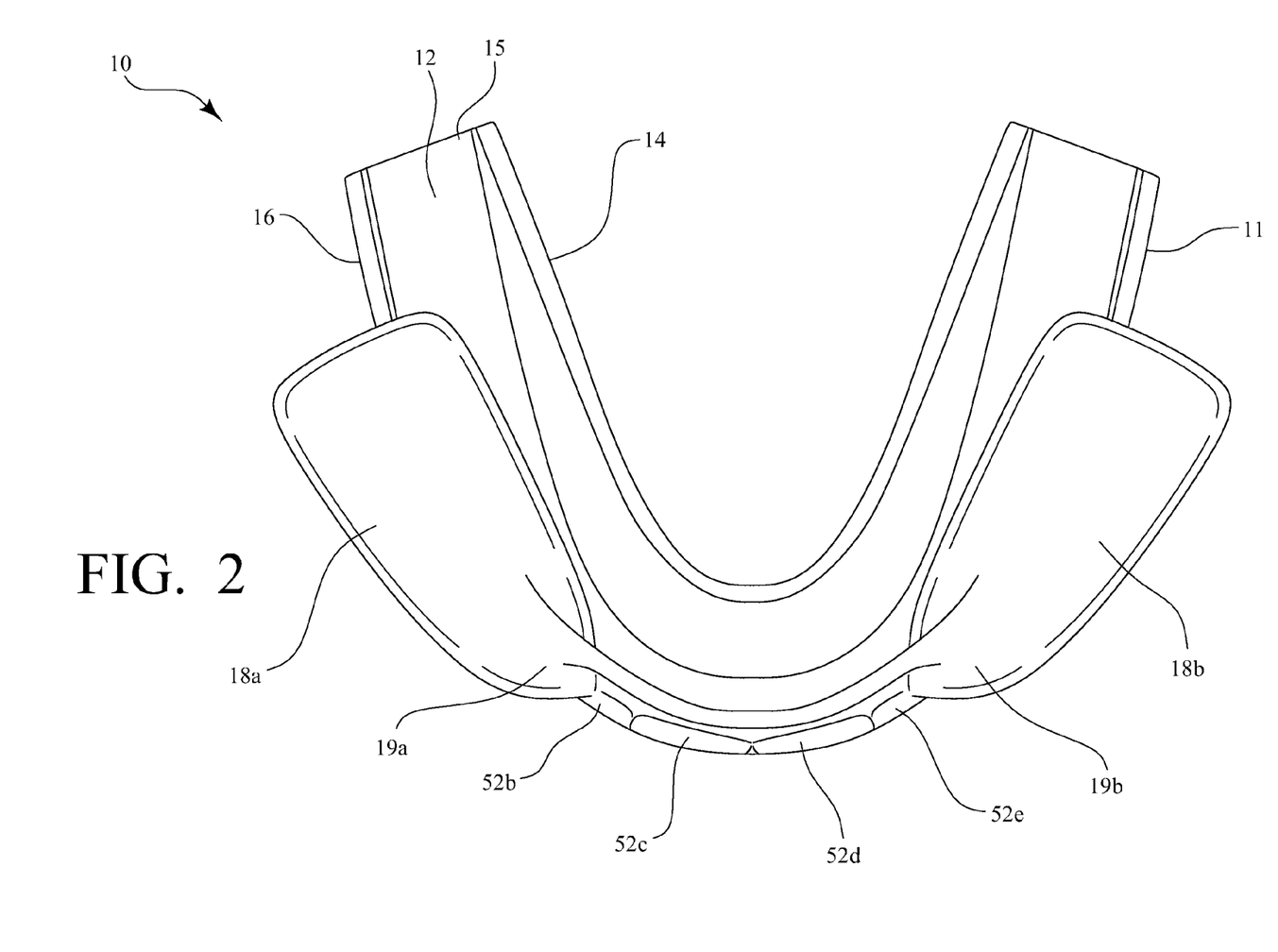
FIG. 2 is a top view of the breathing device of FIG. 1.
Figure 3:
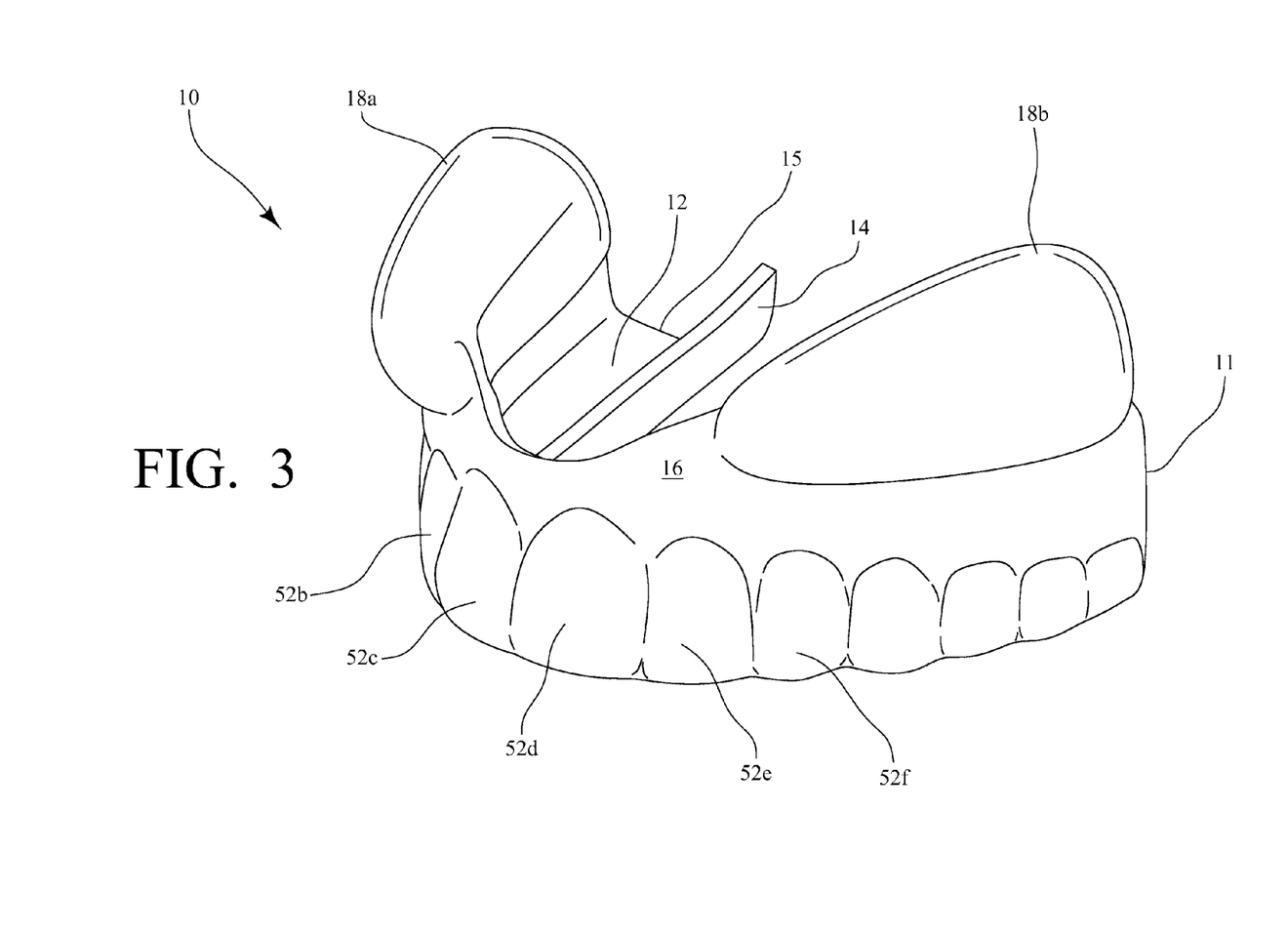
FIG. 3 is a perspective view of the breathing device of FIG. 1.

As shown in FIGS. 1, 2 and 3, a preferred embodiment of a breathing device 10 of the present invention is shown. In the embodiment of FIGS. 1, 2 and 3, the breathing device 10 includes a mouthpiece 11 of generally U-shaped configuration with an inner wall 14 and an outer wall 16. The inner wall 14 and outer wall 16 define a U-shaped channel member 12 which is curved in an arch to conform to a user's 50 (FIG. 4) upper dentition or maxilla 52. (The use of the term maxilla or dentition includes natural teeth, edentulous arch without teeth, or any prosthetic device.) In the preferred breathing device 10, the mouthpiece 11 is molded so that each tooth, edentulous ridge, or any other prosthetic device is received in designated areas of the mouthpiece 11. For example, area 52a aligns with the right maxillary canine, area 52b aligns with the right maxillary lateral incisor, area 52c aligns with the right central incisor, area 52d aligns with the left central incisor, area 52e aligns with the left maxillary lateral incisor, area 52f aligns with the left maxillary canine, area 52g aligns with the second bicuspid, area 52h aligns with the first molar, and area 52i aligns with the second molar. (Even though only the left side of the breathing device is shown in FIG. 3, it is realized that the right side is symmetrical). The spacing between the inner wall 14 and outer wall 16 is defined by horizontally extending platform member 15 which is of sufficient width to receive the user's 50 upper dentition 52, therebetween. Moreover, the U-shaped channel member 12 has a depth slightly greater than the vertical dimension of the user's upper dentition 52.

Figure 7:
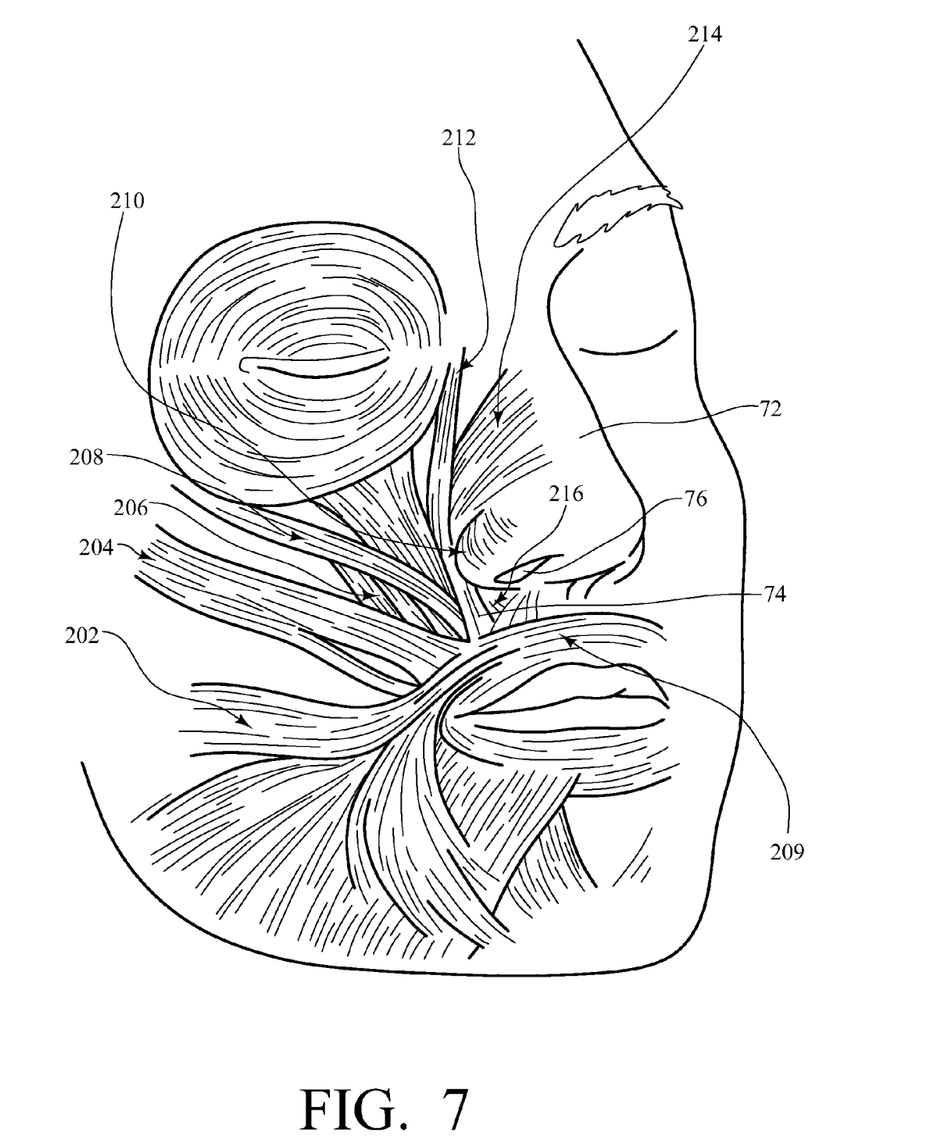
FIG. 7 is an illustration of the facial features including the facial muscles relevant to the use of a mouthpiece breathing device of the present invention; and, FIG. 8 is an interior view of the mouth and nose area illustrating relevant portions of the mouth and breathing device of the present invention in a functional condition.

A pair of nasal passage expansion members 18a, 18b are disposed along opposed sides of the U-shaped outer wall 16. The nasal passages expansion members 18a, 18b may be of any general configuration and are shown as being of cylindrical configuration with tapered mesial expansion terminating ends 19a, 19b, respectively, and rounded distal terminating ends 17a, 17b, respectively, but may be of any other configuration adaptable to engage the area of the muco-buccal vestibule 70 (FIG. 5) between the maxilla 52 and the muscles of facial expression 74 (FIG. 7). Moreover, as best shown in FIG. 1, the mesial expansion member ends 19a, 19b terminate in a distal extent of the vertical alignment with the maxillary lateral incisors 52b and 52e, respectively. Preferably, the terminating ends 19a, 19b align between the vertically extending central axis of the distal extent of the maxillary lateral incisors 52b, 52e, and the vertical extending axis of the mesial extent of the maxillary canines 52a and 52f. Furthermore, distal terminating ends 17a, 17b terminates in the area between the mesial extent of the upper first molar as exemplified by first molar 52g in FIG. 3 and the distal terminating end of the upper maxillary ridge. Preferably, the distal terminating ends 17a, 17b will depend upon the facial anatomy of the user.

The breathing device 10 is generally of unitary construction and may be constructed of any well known materials utilized in the making of commercial mouthpieces, and the like, which are commonly worn by athletes in contact sports. Particularly, the breathing device 10 may be made of polyethylene teraphathalate, polyethylene, polypropylene, rubber or the like. And, as depicted in FIGS. 1, 2, 3, breathing device 10 is molded to conform to the upper dentition, edentulous ridge, or any prosthetic device of a user 50 (FIG. 4).

Figure 4:
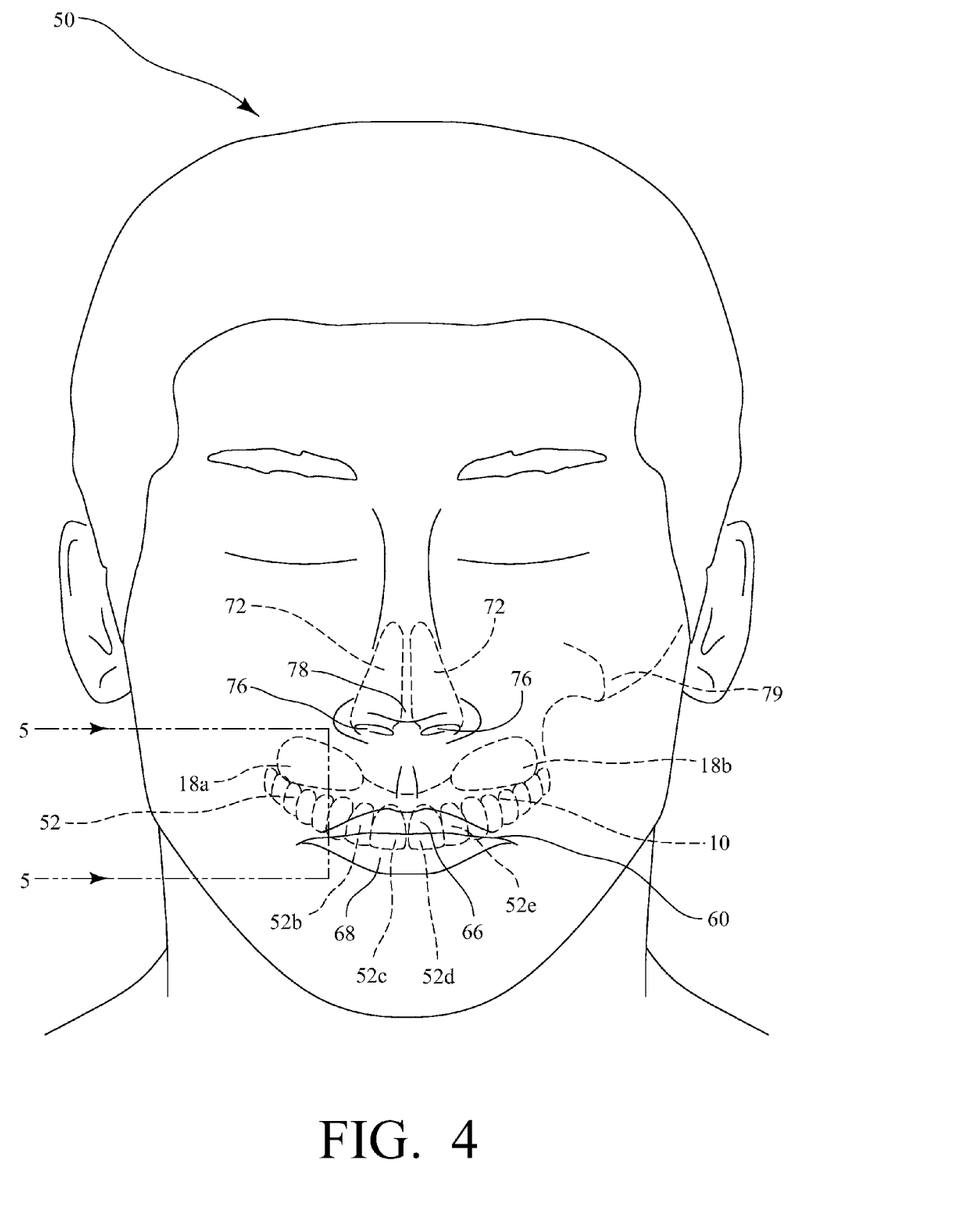
FIG. 4 is an illustration of the breathing device of FIG. 1 in a use condition with selected sections shown in phantom lines.
Figure 5:
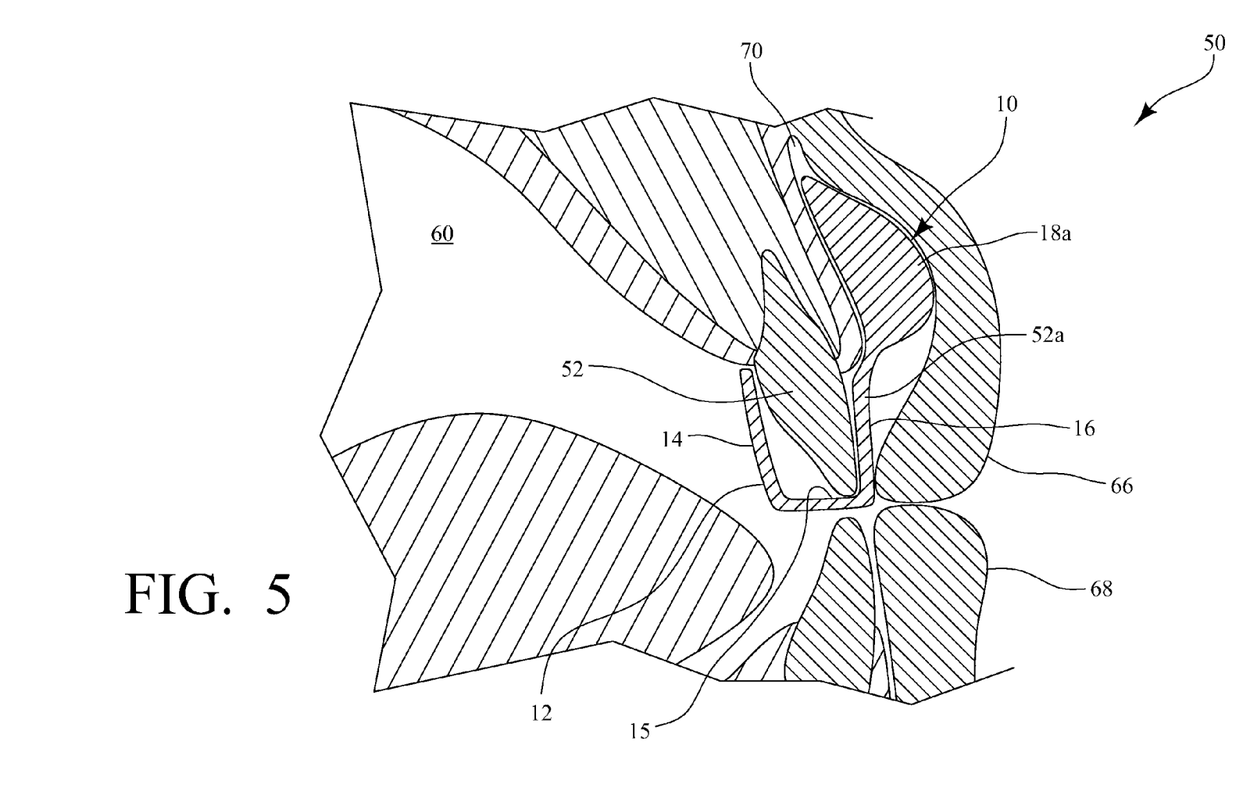
FIG. 5 is a sectional view taken along lines 5-5 of FIG. 4.

As shown in FIG. 4, a breathing device 10 is shown in a use condition in the mouth 60 of a user 50 wherein the mouthpiece 10 is disposed within the mouth 60 and partially covered by the upper lip 66 and the lower lip 68. As shown in FIG. 5, when the breathing device 10 is positioned within the mouth 60 of a user 50, the nasal passage expansion members 18a and 18b (only portions of expansion member 18a being shown), are disposed along opposed sides of the U-shaped outer wall 16 and extend into the muco-buccal and muco-labial vestibule 70 (FIG. 5) of the user 50 distally from the lateral extent of the nares 76 to the zygoma 79, as shown in FIG. 4, and engage the muscles of facial expression 74 (FIG. 7). Upon engagement of the nasal passage expansion members 18a and 18b with the muco-buccal vestibule 70 and the muscles of facial expression 74 (FIG. 7), the walls of the nasal passages 72 and nares 76 are enlarged. Upon enlargement of the nasal passages 72 and nares 76, the air through the nose 78 (FIG. 4) is increased to the user 50. With the use of the breathing device 10, it has been shown in clinical tests to increase the air flow conductants of up to 33% more air flow into the user's 50 respiratory system.

Figure 8:
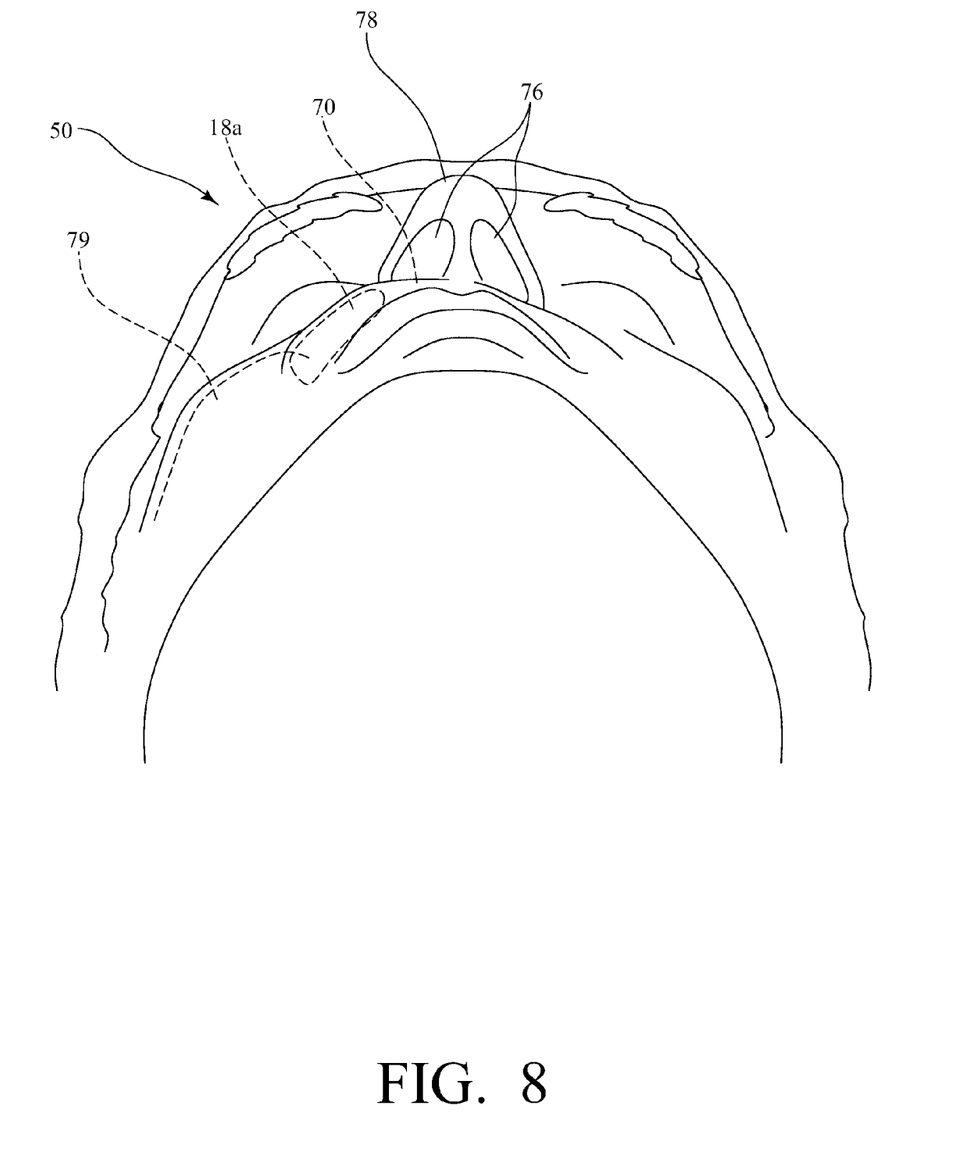

In FIGS. 7 and 8 are shown the muscles of facial expression 74 and the areas of the mouth 60 which are affected by the engagement of nasal passage expanding members 18a, 18b with the muco-buccal and muco-labial vestibule 70. By inserting members 18a, 18b between the maxillary ridge into the muco-labial fold and muco-buccal area, the muscles of facial expression 74 expand bilaterally superiorly and laterally. These include the buccinators 202 which is attached mesially to the obicularis oris 209 to which the nasalis 214, 216, levator anguli oris 206, zygomaticus major 204, zygomataicus minor 208, the levator labii superiors 212, and the dilator naris 210, are also attached. All of these muscles of facial expression 74 are affected by the breathing device 10 labially, superiorly, and buccally achieve tension to distend and open the nares 76 and lateral walls of the nasal canal.

Figure 6:
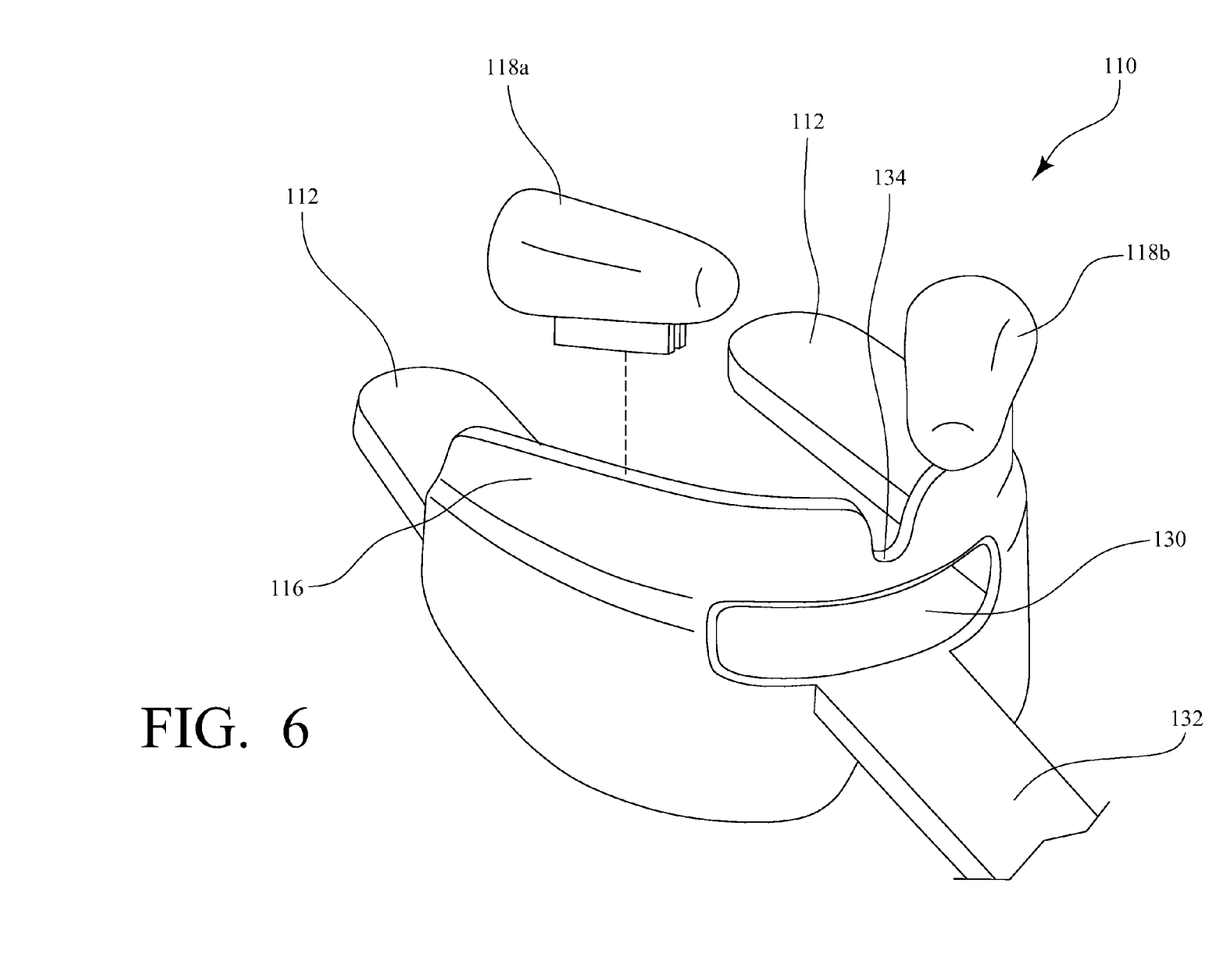
FIG. 6 is a perspective view of another embodiment of the breathing device of the present invention showing vestibule engaging members of the present invention in a detached condition.

In FIG. 6 is shown another embodiment of the present invention. In FIG. 6 a sports mouthpiece 110 is provided with a U-shaped horizontally extending platform 112 which is adapted to receive the upper dentition 52 of a user 50 therein with a wall 116 which is adapted to extend upwardly a distance greater than the vertical dimension of the user's upper dentition 52 on the labial-buccal side. Mouthpiece 110 is also provided with a notch 134 centrally disposed within the wall 116 for engagement with the anterior frenum of a user 50.

Also, an opening 130 is provided therein to accommodate mouth breathing when the mouthpiece 110 is placed in the user's 50 mouth and a handle 132 which extends outwardly from the wall 116 for attachment to a helmet or the like (not shown) may also be provided when worn by athletes in a contact sport. Wall 116 is provided with nasal passage expansion members 118a and 118b on opposite sides of the U-shaped wall 116 for engagement with the muscles of facial expression 74 (FIG. 7) and labial-buccal vestibule 70 in the same manner as the breathing device 10 discussed hereinbefore. Moreover, the expansion members 118a and 118b may be removably attached to the upper portion of the wall 116 and may be attached by any adhesive well known in the art or may include snap-on devices or the like for easy removal and attachment to the breathing device 110.

The detailed description is given primarily for clearness of understanding and no unnecessary limitations are to be understood therefrom for modifications will become obvious to those skilled in the art upon reading this disclosure and may be made without departing from the spirit of the invention and scope of the appended claims.

What is claimed is:

1. A mouthpiece breathing device of one piece unitary construction for intra-oral use molded to conform to a user's upper dentition comprising:
 a molded mouthpiece member of generally U-shaped configuration curved in an arch to conform to a user's upper dentition, the mouthpiece member having at least one U-shaped wall with a receptacle to receive said user's upper dentition, the at least one U-shaped wall having a depth greater than a vertical dimension of said user's upper dentition;
 a pair of fixed nasal passage expansion members integral with and disposed along opposed sides of said mouthpiece member are positioned to extend into a muco-labial and muco-buccal vestibule of said user distally from the lateral extent of the nares to the zygoma and engage the muscles of facial expression whereby upon insertion into the mouth of a user, walls of the nasal passages and nares are enlarged.

2. The breathing device of claim 1, said mouthpiece member being a U-shaped channel member curved in an arch to conform to a user's upper dentition, said channel member having an inner U-shaped wall and an outer U-shaped wall with a spacing between said inner and said outer wall sufficient to receive said user's upper dentition therebetween, said U-shaped channel on the labial-buccal side having a depth greater than a vertical dimension of said user's upper dentition.

3. The breathing device of claim 1, wherein said mouthpiece member includes an outer wall attached to a horizontally extending platform of U-shaped configuration, said U-shaped platform disposed to receive a user's upper dentition and the outer wall has a depth greater than a vertical dimension on the labial-buccal side of a user's dentition.

4. The breathing device of claim 1, said expansion members having a first mesial expansion terminating end between the vertical alignment of the distal extent of maxillary lateral incisors of a user and the vertical alignment of the mesial extent of maxillary canines of a user.

5. The breathing device of claim 4, said expansion members having an expansion member distal terminating end disposed to be positioned between the mesial extent of an upper first molar and a distal terminating end of an upper maxillary ridge of a user.

6. The breathing device of claim 1, said expansion members having a first mesial expansion terminating end at the lateral extent of the nares of a user.

* * * * *